US009526853B2

(12) United States Patent
Refsland et al.

(10) Patent No.: US 9,526,853 B2
(45) Date of Patent: Dec. 27, 2016

(54) VENTILATION SYSTEM (75) Inventors: Earl Refsland, St. Louis, MO (US); Kevin Kroupa, St. Louis, MO (US)

(73) Assignee: Allied Healthcare Products, Inc., St. Louis, MO (US)

( * ) Notice: Subject to any disclaimer, the term of this patent is extended or adjusted under 35 U.S.C. 154(b) by 970 days.

(21) Appl. No.: 13/233,823

(22) Filed: Sep. 15, 2011

(65) Prior Publication Data
US 2012/0060840 A1 Mar. 15, 2012

Related U.S. Application Data (60) Provisional application No. 61/383,225, filed on Sep. 15, 2010.

(51) Int. Cl.
*A61M 16/00* (2006.01)
(52) U.S. Cl.
CPC .. *A61M 16/0051* (2013.01); *A61M 2016/0021* (2013.01); *A61M 2016/0027* (2013.01); *A61M 2016/0036* (2013.01); *A61M 2205/33* (2013.01); *A61M 2205/50* (2013.01); *A61M 2205/502* (2013.01); *A61M 2205/8206* (2013.01)
(58) Field of Classification Search
CPC .............. A61M 16/00; A61M 16/0003; A61M 16/0051; A61M 16/0072; A61M 16/006; A61M 16/1005; A61M 16/20; A61M 16/201; A61M 16/202; A61M 2205/33; A61M 2205/3327; A61M 2205/3331; A61M 2205/3334; A61M 2205/3344; A61M 2205/50; A61M 2230/005; A61M 2230/40

USPC ......... 128/204.21, 200.24, 203.12, 204.18,128/204.22, 204.23, 204.26
See application file for complete search history.

(56) References Cited

U.S. PATENT DOCUMENTS

| | | | |
|---|---|---|---|
| 5,692,497 A | 12/1997 | Schnitzer et al. | |
| 5,915,380 A | 6/1999 | Wallace et al. | |
| 6,390,091 B1 | 5/2002 | Banner et al. | |
| 6,526,970 B2 | 3/2003 | Devries et al. | |
| 6,571,796 B2 * | 6/2003 | Banner et al. | 128/204.26 |
| 7,188,621 B2 | 3/2007 | Devries et al. | |
| 8,707,954 B2 * | 4/2014 | McCarthy | 128/205.23 |
| 2001/0035186 A1 * | 11/2001 | Hill | 128/204.18 |
| 2002/0104537 A1 | 8/2002 | Banner et al. | |
| 2003/0010339 A1 | 1/2003 | Banner et al. | |
| 2008/0041380 A1 | 2/2008 | Wallace et al. | |
| 2008/0072902 A1 * | 3/2008 | Setzer et al. | 128/204.21 |
| 2010/0083968 A1 | 4/2010 | Wondka et al. | |
| 2010/0218766 A1 | 9/2010 | Milne | |
| 2011/0138315 A1 * | 6/2011 | Vandine et al. | 715/780 |

OTHER PUBLICATIONS

International Search Report, Dec. 21, 2011, in International Application No. PCT/US2011/051778.
(Continued)

*Primary Examiner* — Justine Yu
*Assistant Examiner* — Colin W Stuart
(74) *Attorney, Agent, or Firm* — Polsinelli PC (57) ABSTRACT A ventilation system having a processor in communication with a mechanical ventilator and a user interface for allowing an individual to operate the system with little or no respiratory care expertise until a respiratory care practitioner can take over operation is disclosed. The ventilation system further includes a function that permits seamless transition between modes of operation.

22 Claims, 8 Drawing Sheets
(7 of 8 Drawing Sheet(s) Filed in Color)

(56) References Cited

OTHER PUBLICATIONS

First Examination Report regarding Australian Patent Application No. 2011301986 issued Jun. 3, 2014, 5 pages.
European Search Report regarding European Patent Application No. 11825944.9 issued Sep. 9, 2014, 10 pages.
Australian Patent Examination Report No. 2 for Patent Application 2011301986, dated Jun. 2, 2015, 4 pages.
Translation of Official Action relating to Mexican Patent Application No. MX/a/2013/002835, dated Nov. 10, 2015. 4 pages.
Translation of Official Action relating to Russian Patent Application No. 2013116800, dated Nov. 11, 2015. 6 pages.
English translation of Japanese Office Action issued Jun. 20, 2015 in corresponding application. 3 pages.
Office Action issued Sep. 16, 2015 in corresponding Russian Application No. 2013116800. 8 pages.

* cited by examiner

VENTILATION SYSTEM

CROSS REFERENCE TO RELATED APPLICATIONS

This is a non-provisional patent application and claims priority to U.S. Provisional Patent Application Ser. No. 61/383,225, filed on Sep. 15, 2010, which is herein incorporated by reference in its entirety.

FIELD

The present disclosure relates to a ventilation system, and in particular to mechanical ventilator system having different modes of operation that permits operation by either a non-expert or an expert to provide mechanical ventilation to a patient.

BACKGROUND

In medicine, mechanical ventilation is a method to mechanically assist or replace spontaneous breathing of a patient using a machine called a ventilator. Mechanical ventilation is often a life-saving intervention, but carries many potential complications including pneumothorax, airway injury, alveolar damage, and/or ventilator-associated pneumonia, thereby requiring that a respiratory care practitioner operate the ventilator.

The delivery of a "gold standard" of care in mechanical ventilation to a patient population relies on having a sufficient number of acute care ventilators on hand as well as a requisite number of respiratory care practitioners to properly operate them. Recognizing that in a severe pandemic like the 1918 Spanish Flu pandemic, or a mass casualty event, such as a major earthquake, hurricane, or terrorist incident, the very real possibility exists that patient loads generated by such events will initially exceed the number of stockpiled ventilators and/or the requisite number of respiratory care practitioners on hand to provide even a modified gold standard treatment to a large number of patients requiring mechanical ventilation. Even if a sufficient number of mechanical ventilators are stockpiled in a particular area, the large number of immediate casualties in such a catastrophic event could overwhelm the limited number of respiratory care practitioners available to provide the necessary expertise to operate all of the ventilators required to treat a large number of patients, especially those patients not being treated by emergency personnel or at a healthcare facility, such as a hospital. Accordingly, there is a need for a ventilation system that may be operated by a non-expert with no or little experience in the operation of a ventilator as well as a ventilator adapted for seamless adjustment of ventilator functions and parameters by a respiratory care practitioner. There is also a need for a ventilation system having various modes of operation that can be utilized to mechanically ventilate patients outside a hospital setting without an AC power source.

SUMMARY

In one embodiment, a ventilation system may include a mechanical ventilator for providing a mechanical ventilation function based on a plurality of volumetric and pressure-related parameters with the mechanical ventilator being adapted to detect a signal representative of at least one of the plurality of volumetric and pressure-related parameters. A processor is in operative communication with the mechanical ventilator for receiving the detected signal to adjust one or more of the plurality of volumetric and pressure-related parameters of the mechanical ventilator. A user interface is in operative communication with the processor for allowing adjustment of the one or more of the plurality of volumetric and pressure-related parameters, wherein the processor automatically adjusts at least another one or more of the plurality of volumetric and pressure-related parameters based on the detected signal.

A method for using a ventilation system including:
providing a ventilation system that may include a mechanical ventilator including a means for providing a mechanical ventilation function based on a plurality of volumetric and pressure-related parameters, the mechanical ventilator being adapted to detect a signal representative of at least one of the plurality of volumetric and pressure-related parameters; a processor in operative communication with the mechanical ventilator for receiving the detected signal, and a user interface in operative communication with the processor for displaying and adjusting values of the volumetric and pressure-related parameters;
detecting a signal representative of at least one of the plurality of volumetric and pressure-related parameters by the processor; and
adjusting one of the plurality of volumetric and pressure-related parameters based on the detected signal.

Additional objectives, advantages and novel features will be set forth in the description which follows or will become apparent to those skilled in the art upon examination of the drawings and detailed description which follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Corresponding reference characters indicate corresponding elements among the view of the drawings. The headings used in the figures should not be interpreted to limit the scope of the claims.

DETAILED DESCRIPTION

A population center that has suffered a mass casualty event, such as an earthquake, hurricane, flu pandemic or terrorist incident can produce injuries that result in a large number of patients requiring immediate treatment, thereby initially placing a huge burden on local healthcare and emergency medical resources. In particular, such a mass casualty event can require the use of a large number of ventilators to mechanically ventilate all of the patients requiring immediate care and attention by respiratory care practitioners. However, the expense of stockpiling a large number of ventilators can be cost prohibitive and thereby reduce the number of available ventilators in a particular area. In addition, a sufficient number of respiratory care practitioners qualified to properly operate such mechanical ventilators may be initially unavailable in a mass casualty event to render immediate treatment, thereby leaving only individuals with no respiratory care expertise to potentially operate the mechanical ventilator and provide unassisted mechanical ventilation to a patient.

As such, a ventilation system as described herein improves on such mechanical ventilators by providing a ventilation system that can be operated by an individual with no respiratory care expertise to initiate operation of the ventilator until a respiratory care practitioner can attend to the patient. It would also be desirable to provide such a ventilation system having improved functionalities for use and operation by the practitioner.

Figure 1:
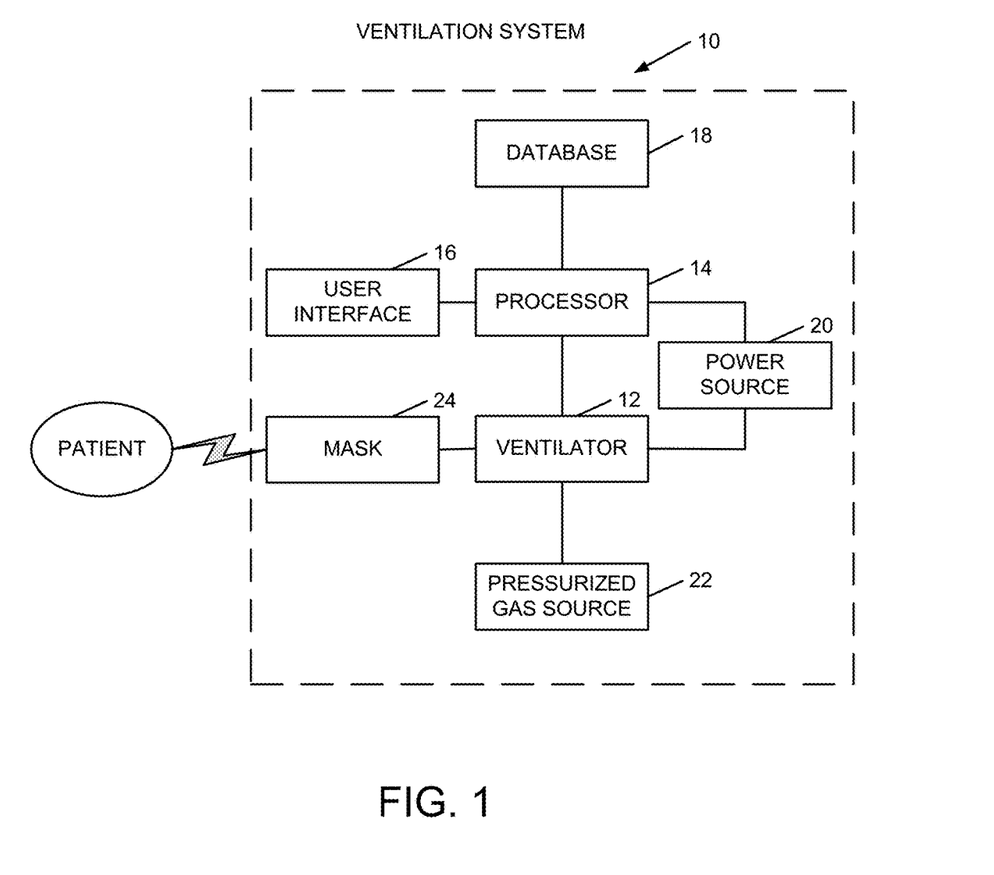
FIG. 1 is a simplified block diagram showing one embodiment of the basic components for a ventilation system.

Referring to the drawings, an embodiment of the ventilation system is illustrated and generally indicated as 10 in FIG. 1. In general, the ventilation system 10 includes a mechanical ventilator 12 for providing mechanical ventilation to a patient (not shown) in response to a processor 14 that controls the operation of the mechanical ventilator 12. In one embodiment, the mechanical ventilator 12 may be attached to a mask 24 configured to be secured over the face of a patient for providing ventilation to the patient's airway. In addition, other types of devices, such as an endotracheal tube, may be used instead of the mask 24. The mechanical ventilator 12 may further include a pressurized gas source 22 that provides pressurized gas to mechanically ventilate the patient's lungs. In one embodiment, the pressurized gas source 22 may be a low-pressure oxygen source system. In addition, the processor 14 communicates with a database for storing data and a user interface 16 for providing an operational platform for the individual to view displayed data and information, adjust ventilator functionalities, and monitor certain ventilation parameters as shall be described in greater detail below.

As further shown, a power source 20 provides power to the mechanical ventilator 12 including the processor 14 and user interface 16. In one embodiment, the power source 20 may be an AC power source, or in the alternative the power source 20 may be a battery, such as a lead acid battery, lithium-ion battery and NiCad battery.

Figure 8:
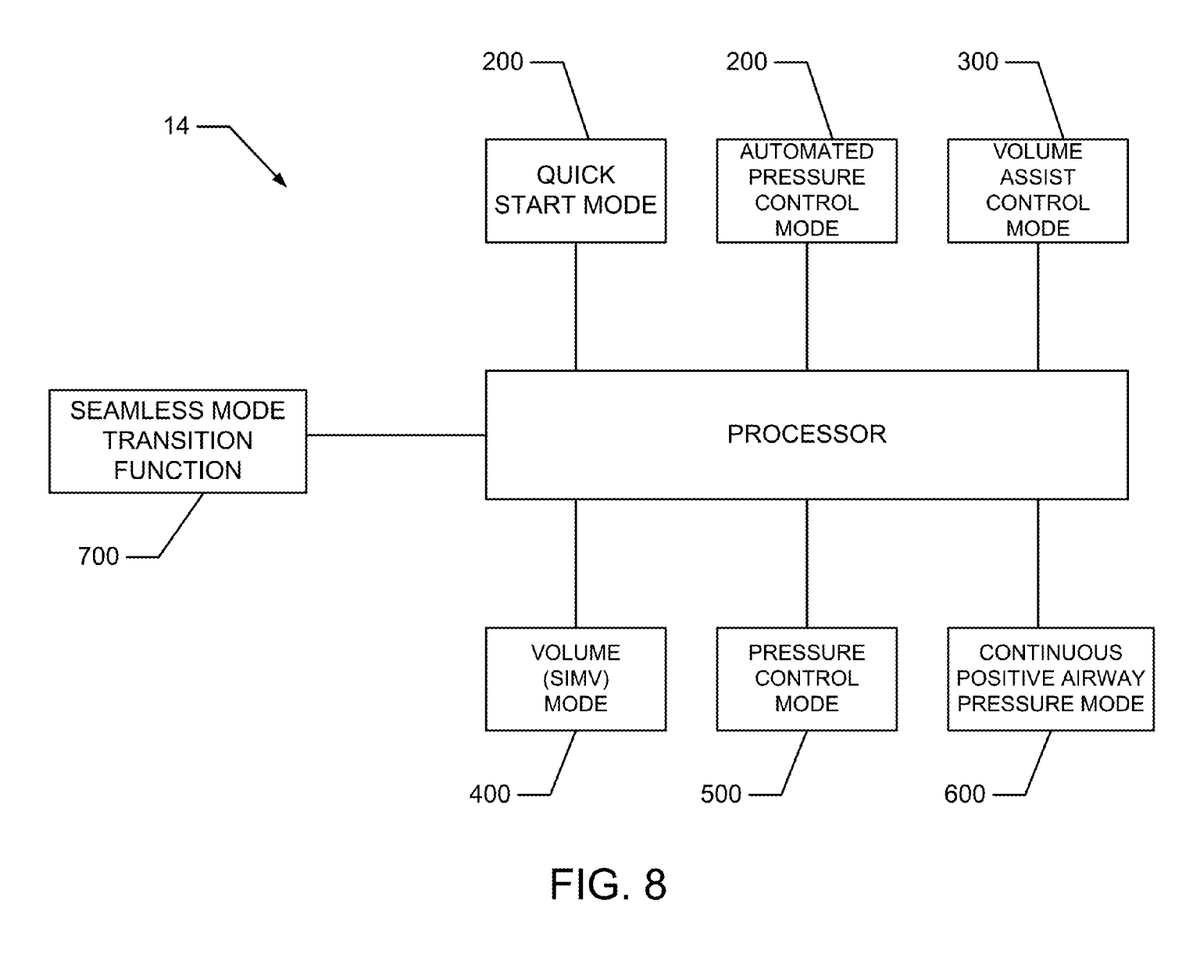
FIG. 8 is a simplified block diagram showing the various modes of operation and functionalities of the ventilation system.

Referring to FIG. 8, the ventilation system 10 may include different modes of operation and functionalities controlled by the processor 14. In one embodiment, the processor 14 may initiate the following modes of operation: Quick Start mode 100, Automated Pressure Control mode 200, Volume Assist Control mode 300, Volume (SIMV) mode 400, Pressure Control mode 500, and Continuous Positive Airway Pressure (CPAP) mode 600. In addition, the processor 14 may initiate a Seamless Mode Transition function 700 to provide seamless transition from one mode of operation to another mode of operation as shall be discussed in greater detail below.

Figure 2:
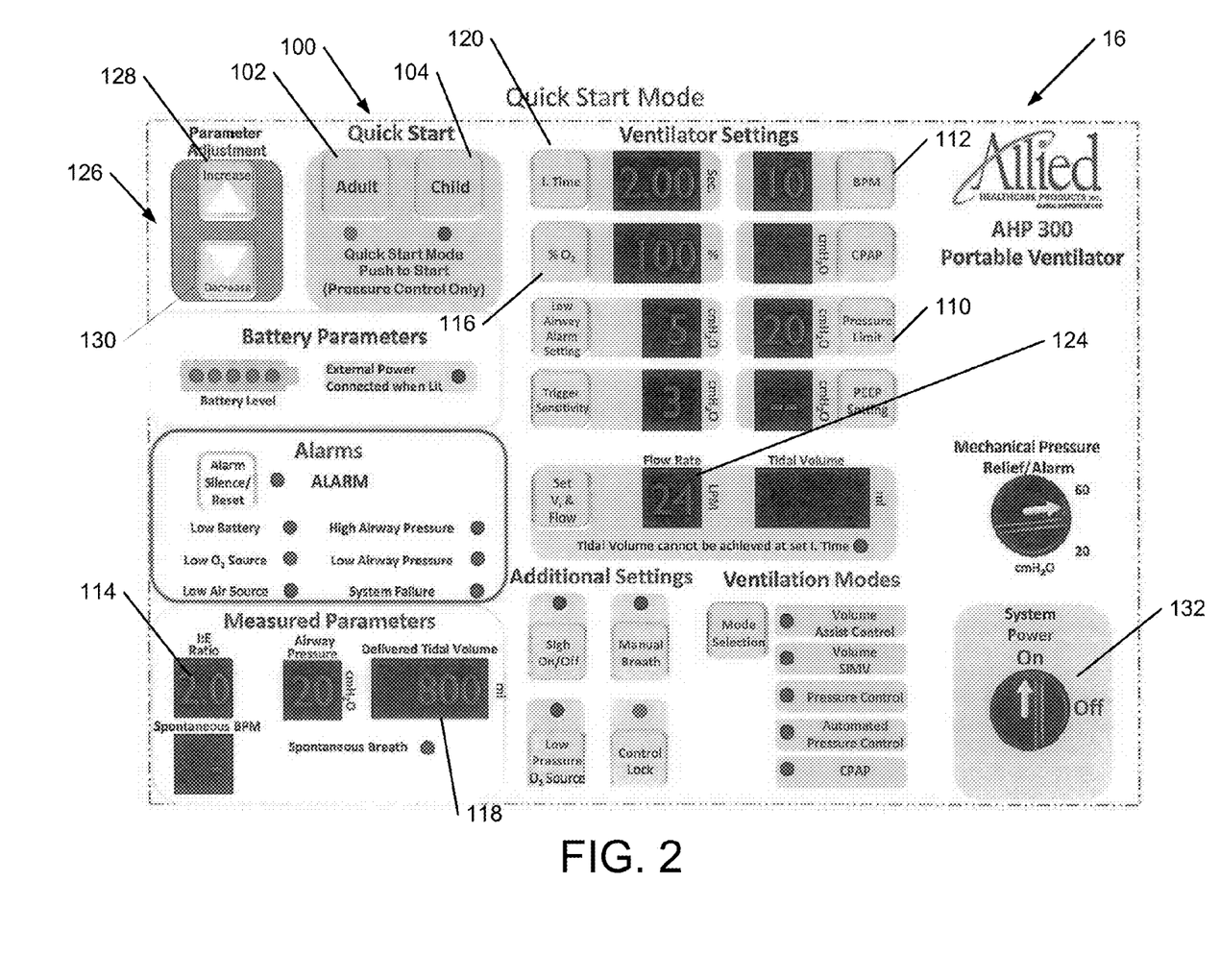
FIG. 2 is a layout of a user interface illustrating the operation of a quick start mode for the ventilation system.

In one aspect of the ventilation system 10 illustrated in FIG. 2, the user interface 16 may include a "Quick Start" mode 100 such that an individual with no respiratory care experience can operate the ventilator 12 and initiate mechanical ventilation to the patient through a single step operation that allows the mechanical ventilator 12 to operate on automatic pilot using preset values for one or more ventilator parameters. After the individual selects either the ADULT Quick Start Mode button 102 adapted to provide preset mechanical ventilation to the typical adult or a CHILD Quick Start mode button 104 to provide preset mechanical ventilation to a typical child, the individual secures the mask 24 to the patient using default settings for particular parameters stored in the database 18. When the individual actuates the Quick Start mode 100, the processor 14 may initiate the Automated Pressure Control mode 200 of operation for the ventilation system 10. In the Automated Pressure Control mode 200 certain pressure-related parameters of the mechanical ventilator 12 are preset by the processor 14 and may be subsequently automatically adjusted by the processor 14 or manually adjusted by the practitioner after certain measurements are made. If manually adjusted, the practitioner may use the parameter adjustment function 126 on the user interface 16 by actuating either the increase button 128 or the decrease button 130.

In one embodiment, the default settings for the Quick Start mode 100 may include the following parameters: Maximum Pressure ("$P_{max}$") 110, Breaths Per Minute ("BPM") 112, Inspiratory-Expiratory Ratio (I-E ratio) 114 and Percentage Oxygen (% $O_2$) 116. In one aspect, the parameters for the ADULT Quick Start mode may have the following preset values: $P_{max}$=15 cmH$_2$O—60 cmH$_2$O range; BPM=6-15 Breaths per Minute range; I-E ratio=1:2 and % $O_2$=100%, while the parameters for the CHILD Quick Start mode may have the following values: $P_{max}$=15 cmH$_2$O-60 cmH$_2$O range; BPM=15-60 Breaths per Minute range; I-E ratio=1:2 and % O2=100%. In one embodiment, the $P_{max}$ default value of 20 cmH$_2$O may be used, which is based on a broadly accepted dictum that this level of pressure is the highest to which an unprotected adult airway should be subjected. Empirically, the medical community has determined that at levels higher than 20 cm H$_2$O some of the mechanically driven gas from the pressurized gas source 22 may migrate down the esophagus and into the stomach, which is undesirable since it can induce vomiting in the patient. In addition, the BPM 112 rate of 10 breaths per minute for adults and 18 BPM 112 rate for children under the Quick Start Mode 100 is based on the widely accepted ranges for mechanical ventilation of such patient types, while the 100% oxygenation rate 110 reflects the normal protocol, normally applied when beginning a patient on ventilation.

Under the Quick Start Mode 100, the first breath is delivered to the patient at a predetermined Flow Rate 124, such as 24 liters per minute, and a signal generated that is representative of the patient's Tidal Volume 118 that indicates the maximum volume the patient's lungs will safely accept. As used herein the term "Tidal Volume" means the maximum amount (volume) of gas taken in by the patient's lungs during each breath. Once the Tidal Volume 118 is determined by detection of the signal received by the processor 14, the ventilation system 10 may automatically adjust the Flow Rate 124 of gas being delivered to the patient in order to achieve the targeted I-E ratio of 1:2 in view of the patient's present Tidal Volume 118. In the Quick Start mode 100, the mechanical ventilator 12 will continuously adjust the Flow Rate 124 when the lung compliance of the patient changes over time according to the detected Tidal Volume 118. As such, continued detection of the patient's Tidal Volume 118 allows the ventilation system 10 to adjust the Flow Rate 124 to maintain the values of BPM 112, I-E ratio 114, and $P_{max}$ 110 preset by the processor 14 when the ventilation system 10 is in the Quick Start mode 100. In addition, detection of the patient's Tidal Volume 118 allows the ventilation system 10 to treat a wide range of different patients and patient conditions by permitting the Flow Rate 124 to be automatically adjusted in view of the patient's contemporaneous physiological characteristics, such as present lung compliance and lung capacity. The capability to automatically adjust one or more parameters when an individual with no respiratory care expertise initiates treatment is important when treating patients whose condition can change in the short term, such as smoke inhalation victims. For example, a smoke inhalation victim may initially have non-compliant lungs due to tissue damage but whose lungs slowly become more compliant over the short term as treatment continues, thereby requiring different parameters for mechanical ventilation. In addition, a patient who appears outwardly normal, but is a long term smoker with non-compliant lungs, may require different initial treatment that requires adjustment of certain parameters over time. As such, the ventilation system 10 has the capability to automatically tailor treatment based on the patient's detected condition without the need for manual intervention.

Since the ventilation system 10 permits adjustments to one or more parameters after the Quick Start mode 100 has been initiated, the ADULT and CHILD Quick Start buttons 102 and 104 are disabled by the processor 14 after the patient's first breath is detected to prevent subsequent actuation of the Quick Start buttons 102 and 104, which can cause one or more of these adjusted parameters to revert back to the preset values of the Quick Start mode 100 if a respiratory care practitioner has made manual adjustments to certain parameters. In one embodiment, restarting the Quick Start mode 100 after disablement requires the individual to manually turn the power button 132 for the power source 20 OFF and then ON again to restart the ventilation system 10 and permit enable the Quick Start mode 100.

Figure 3:
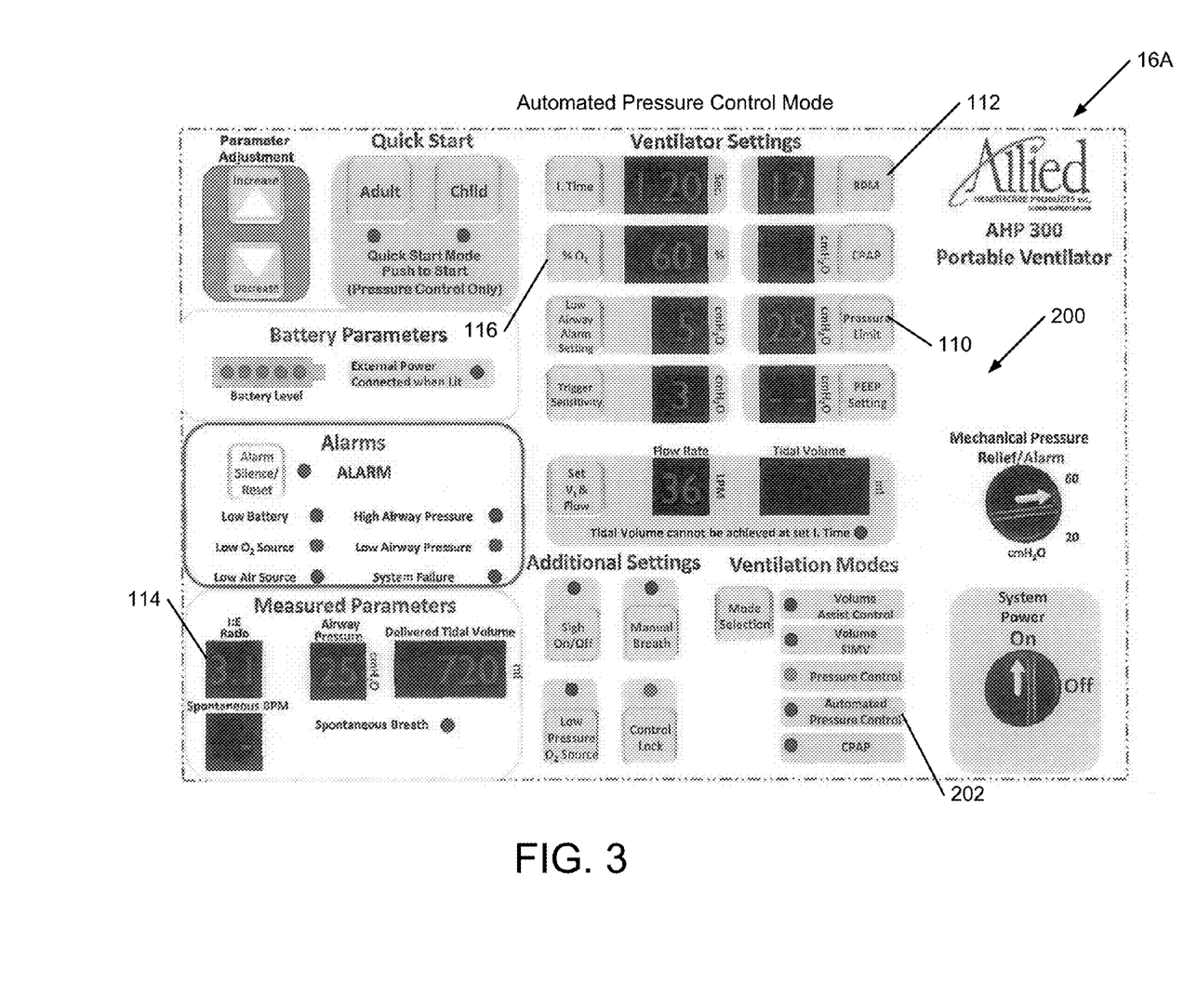
FIG. 3 is a layout of the user interface illustrating the operation of an automated pressure control mode for the ventilation system.

Referring to FIG. 3, the user interface, designated 16A, illustrates the Automated Pressure Control mode 200 of the ventilation system 10 having an Automated Pressure Control mode button 202 which may be actuated to effectuate the Quick Start mode 100. In one embodiment, the preset Flow Rate 124 of 24 liters per minute being delivered to the patient may be automatically adjusted to maintain the BPM 112 value at 10 breaths per minute, an Inspiratory Time 120 of 2.00 seconds and a $P_{max}$ 110 of 20 cmH$_2$O, when the patient Total Volume 118 changes.

Figure 4:
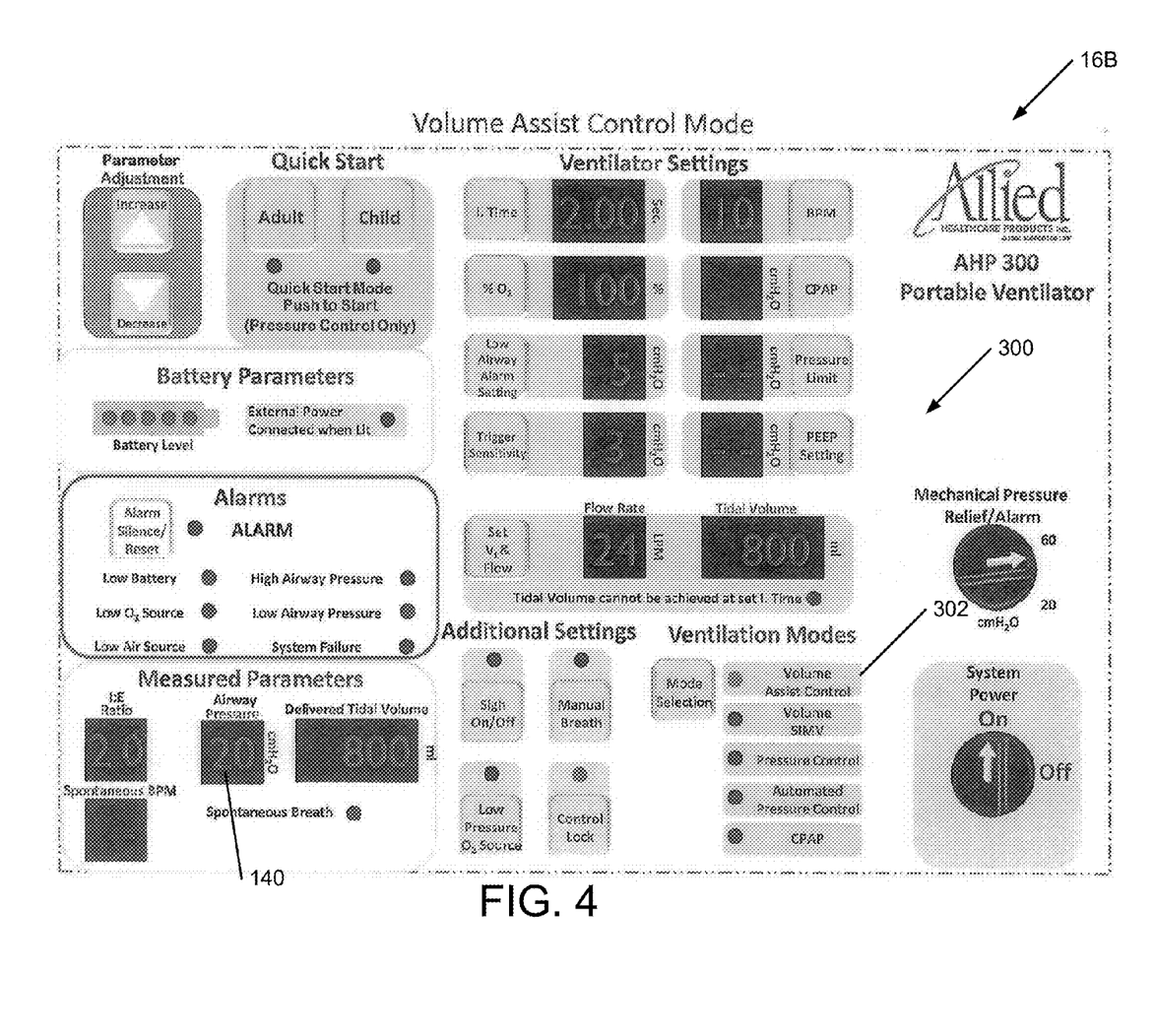
FIG. 4 is a layout of the user interface illustrating the operation of a volume assist control mode for the ventilation system.

As shown in FIG. 4, user interface, designated 16B, illustrates the Volume Assist Control mode 300 having a Volume Assist Control Mode button 302, which is actuated to permit manual entry of values related to BPM 112, Tidal Volume 118, Inspiratory Time 120, and/or O$_2$% 116. In one embodiment, the practitioner monitors the Airway Pressure 140 and the I-E ratio 114 to determine whether to make any adjustments. For example, if the Airway Pressure 140 is too high, the practitioner may lower the Tidal Volume 118, or if the I-E ratio 114 is not in a suitable range, then the Inspiratory Time 120 and/or the BPM 112 may be changed to achieve the desired I-E ratio 114. As such, the Volume Assist Control mode 300 is designed to react to any changes in Inspiratory Time 120 or Tidal Volume 118 by making changes in Flow Rate 124.

Figure 5:
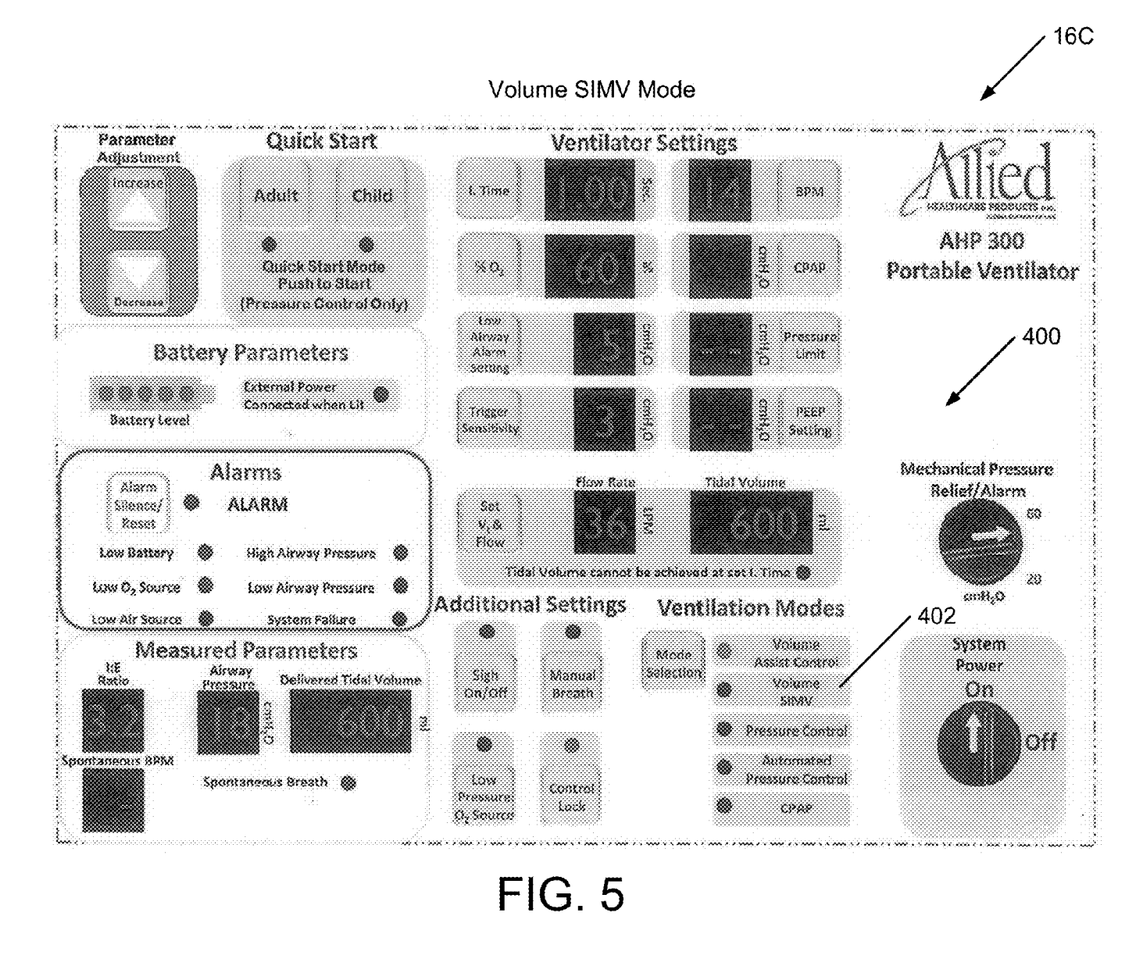
FIG. 5 is a layout of the user interface illustrating the operation of a synchronized intermittent mandatory ventilation mode for the ventilation system.

Referring to FIG. 5, user interface, designated 16C, illustrates the Volume SIMV (Synchronized Intermittent Mandatory Ventilation) mode 400 that may be initiated by actuating a Volume SIMV mode button 402. The Volume SIMV mode 400 may be used when the patient is breathing in either an intermittent fashion or breathing fairly continuously, but with shallow breaths that are not producing a desired Minute Volume (the Tidal Volume 118 of gas exchanged per minute). In such cases, the patient is normally breathing rapidly (e.g., higher than the normal BPM 112) and in a shallow manner (e.g., lower than the normal tidal volume). In this mode, the BPM 112, Tidal Volume 118 and Inspiratory Time 120 are adjusted to achieve the desired Minute Volume and I-E ratio 114. For example, the BPM 112 set at 12 BPM at a Tidal Volume 118 of 700 ml after the Volume SIMV mode 400 is selected. As such, the patient will receive a Minute Volume of 8,400 ml/minute in this setting arrangement.

Figure 6:
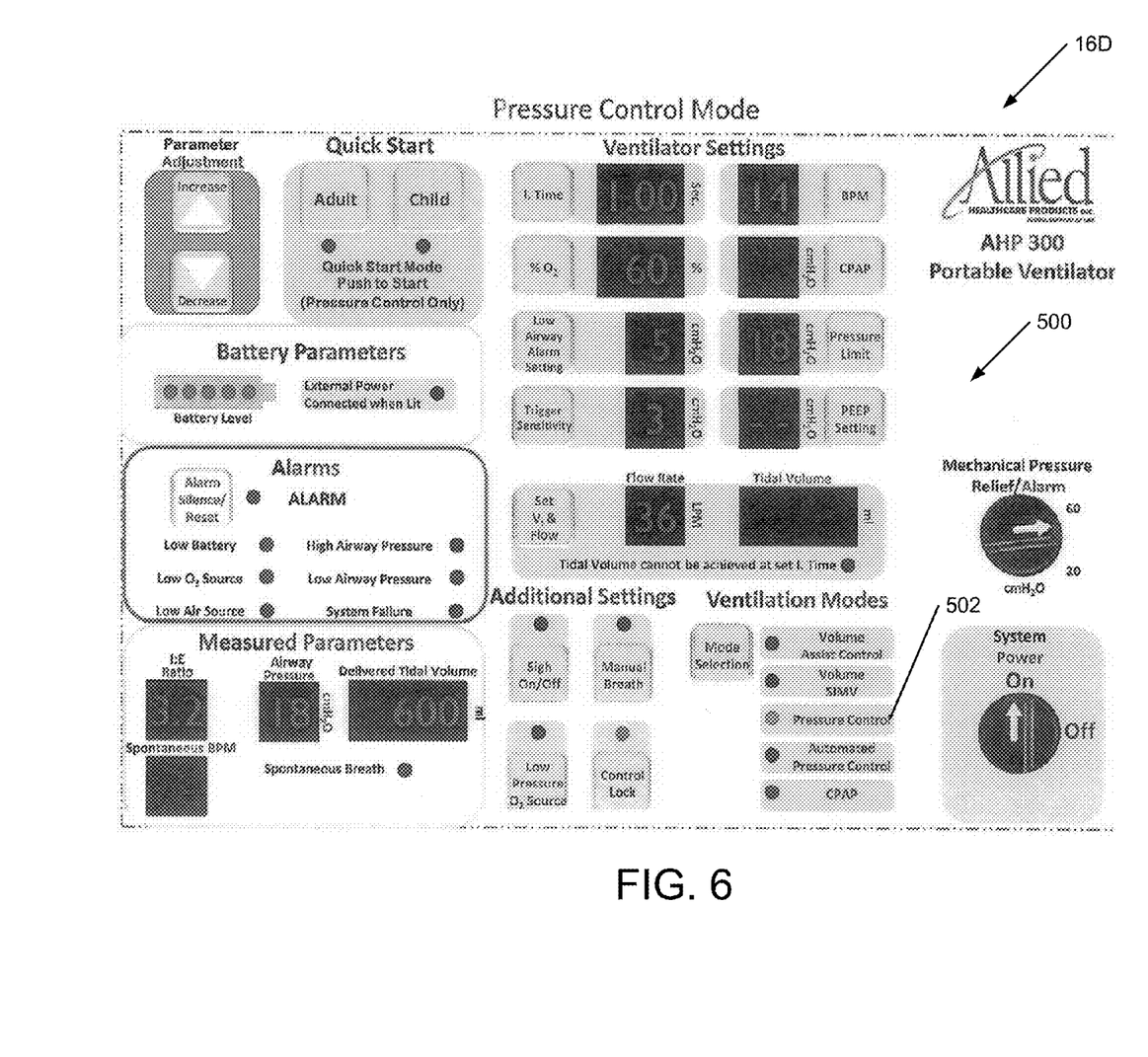
FIG. 6 is a layout of the user interface illustrating the operation of a pressure control mode for the ventilation system.

Referring to FIG. 6, user interface, designated 16D, illustrates the Pressure Control mode 500 that may be initiated by actuating the Pressure Control mode button 502. The Pressure Control mode 500 differs from the other volume-related modes of operation in that the volume control modes, for example the Volume Assist Control mode 300 or Volume SIMV mode 400, allows the practitioner to set the Tidal Volume 118 to be delivered to the patient with each breath. In the Pressure Control mode 500, the practitioner sets the $P_{max}$ 110 that will be generated inside the patient's lungs for each breath. The Tidal Volume 118 to be delivered is a function of the patient's lungs size and compliance (e.g., ability to expand under pressure). The mechanical ventilator 12 will not deliver a larger Tidal Volume 118 than that which will maintain the preset $P_{max}$ 110.

As further shown, the Pressure Control mode button 502 is selected and the practitioner enters the BPM 112, $P_{max}$ 110, and Inspiratory Time 120, which the practitioner estimates will result in the desired I-E ratio 114. For example, if the patient's lungs expand to 400 ml at 20 cm H$_2$O of pressure with the BPM 112 at 10 and a Flow Rate 124 at 10 liters per minute with the goal of achieving an I-E 114 ratio of 1:2. At 10 BPM 112, the respiratory cycle is 6 seconds. Because the patient's lung will expand to 400 ml at a $P_{max}$ of 20 cm H$_2$O, the initial Inspiratory Time 120 for this particular patient will be 2.3 seconds. The following equations may be used to calculate Tidal Volume 118, Inspiratory Time 120 and Flow Rate 124:

$$\text{Tidal Volume} = (\text{Inspiratory Time})(\text{Flow Rate})$$

$$\text{Inspiratory Time} = \text{Tidal Volume}/\text{Flow Rate}$$

$$\text{Flow Rate} = 10 \text{ liters/minute} \times 1 \text{ minute}/60 \text{ seconds} = 0.1667 \text{ liters/second}$$

$$\text{Inspiratory Time} = 0.4 \text{ liters}/0.1667 \text{ liters/second} = 2.3 \text{ seconds}.$$

Given a respiratory cycle of 6 seconds, an Inspiratory Time of 2.3 seconds results in a 3.7 second Expiratory Time and an I-E ratio 114 of 1:1.6. Since an I-E ratio 114 is set at 1:2, the practitioner would increase the Flow Rate 124 to 12 liters per minute to achieve the desired Inspiratory Time 120 of 2 seconds and an I-E ratio 114 of 1:2.

In the Pressure Control mode 500, any of the above parameters may be altered to tailor the mechanical ventilation therapy of the patient. For example, the patient might not be getting the Minute Volume (Tidal Volume×BPM) required for proper oxygenation per the initial preset values. If noted, the practitioner might increase the BPM 112 with accompanying adjustments to Flow Rates 124 and I-E ratios 114.

Figure 7:
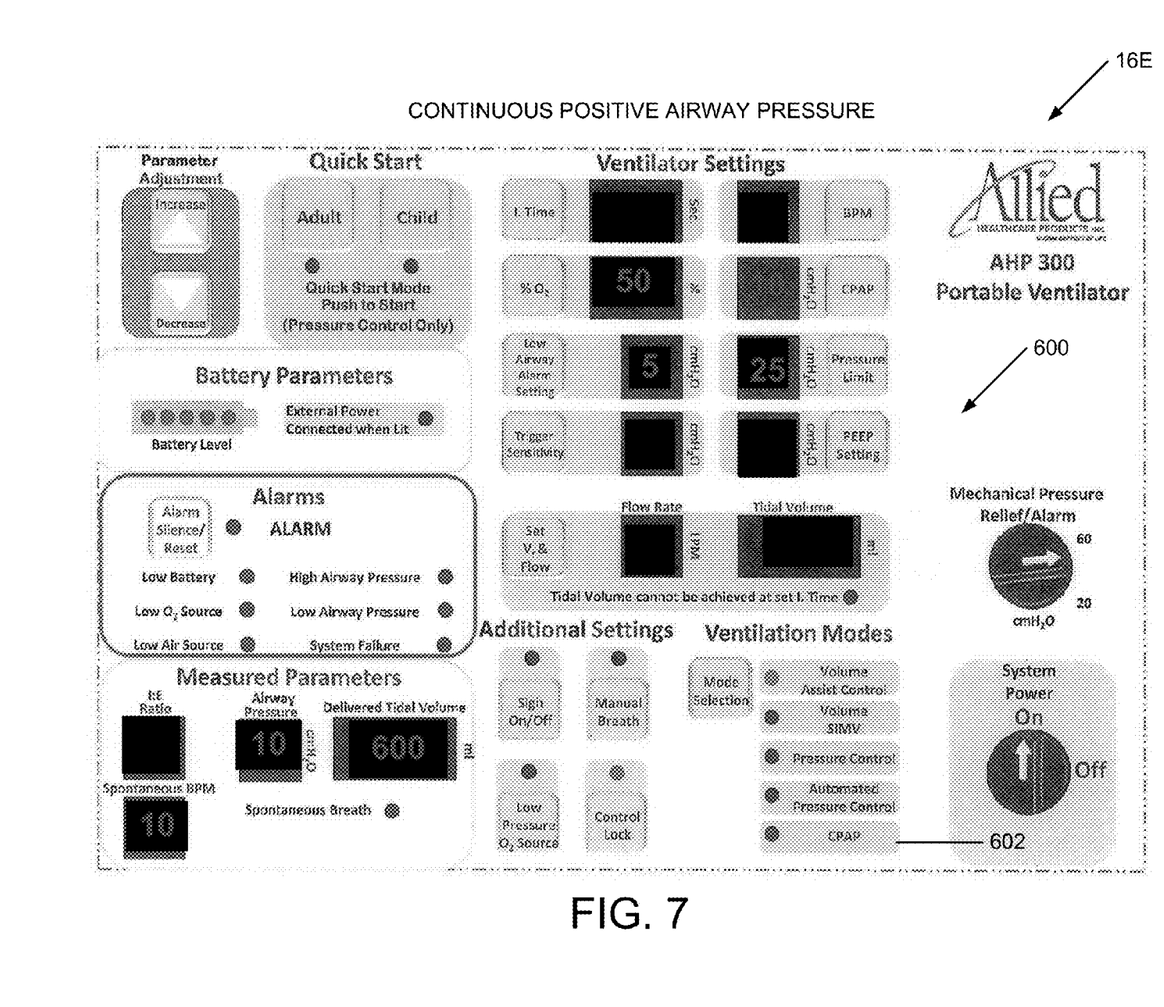
FIG. 7 is a layout of the user interface illustrating the operation of a continuous positive airway pressure mode for the ventilation system.

Referring to FIG. 7, the user interface, designated 16E, illustrates the Continuous Positive Airway Pressure (CPAP) mode 600, which is actuated using the CPAP mode button 602 when the patient being treated is able to breathe without mechanical intervention. The therapy is delivered through the mask 24 secured to the patient, although in other embodiments delivery may be accomplished using an endotracheal tube. In CPAP mode 600, the mechanical ventilator may include a demand valve (not shown) allowing the patient to use his or her own energy to draw in and exhale breaths, but throughout the patient's ventilation cycle the mechanical ventilator 12 maintains a slight positive gas pressure within the closed system comprising the tubing, mask and lungs.

In another aspect shown in FIG. 8, the ventilation system 10 may include a Seamless Mode Transition function 700 automatically performed by the processor 14 that allows a seamless transition between operational modes when the practitioner changes the operational mode of the ventilation system 10 from the Pressure Control mode 500 to either the Volume Assist Control mode 300 or the Volume SIMV mode 400. In other words, the practitioner does not have to manually adjust any of the parameters when changing operational modes of the ventilation system 10 since the processor 14 automatically makes the necessary calculations. For example, in the Pressure Control mode 500 the values for BPM 112, $P_{max}$ 110, and Inspiratory Time 120 are preset such that only the Tidal Volume 118 is measured. When the practitioner switches from the Pressure Control mode 500 to either the Volume Assist Control mode 300 or the Volume SIMV mode 400, the processor 14 automatically determines the values for the Tidal Volume 118 for the new operational mode based on the previous measured values for Tidal Volume 118 when the ventilation system 10 was in the Pressure Control mode 500. As such, the practitioner does not have to make any manual calculations or manually adjust the values for the Tidal Volume 118 when a change in operational mode is made in this manner.

Conversely, in either the Volume Assist Control mode 300 or the Volume SIMV mode 400, the values for Tidal Volume 118 and Inspiratory Time 120 are preset in these modes and $P_{max}$ 110 and Flow Rate 124 are measured, but are not preset in order to maintain a particular Tidal Volume 118. When the practitioner switches from the Volume Assist Control mode 300 or the Volume SIMV mode 400, the processor 14 automatically determines the values for $P_{max}$ 110 and Flow Rate 124 for the new operational mode based on measured values for the $P_{max}$ 110. In other words, the processor 14 makes the necessary conversion and adjustment in values for $P_{max}$ 110 and Flow Rate 124 when changing from a pressure control mode to a volume control mode, while also making the necessary conversion in values for Tidal Volume 118 when changing from a volume control mode to a pressure control mode without the practitioner having to calculate the conversions and enter the converted values.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A ventilation system comprising:
a mechanical ventilator for providing a mechanical ventilation function based on a plurality of volumetric and pressure-related parameters, the mechanical ventilator being adapted to detect a signal representative of at least one of the plurality of volumetric and pressure-related parameters;
a processor in operative communication with the mechanical ventilator for receiving the detected signal, the processor being adapted to adjust one or more of the plurality of volumetric and pressure-related parameters of the mechanical ventilator;
a user interface in operative communication with the processor for allowing adjustment of the one or more of the plurality of volumetric and pressure-related parameters, wherein the processor automatically adjusts at least another one or more of the plurality of volumetric and pressure-related parameters based on the detected signal; and
a quick start mode operated by the processor with the quick start mode including preset mechanical ventilation parameters for initiating the mechanical ventilation function, the quick start mode configured to allow a non-clinician individual with no respiratory care expertise to initiate the mechanical ventilation function automatically through a single step operation, wherein the quick start mode is initiated by the non-clinician individual through the single step operation and operated without assistance by a clinician,
wherein the processor disables the quick start mode after a first breath of a patient is detected by the processor to prevent the quick start mode from actuating parameters specific to the quick start mode after the first breath of the patient has been detected.

2. The ventilation system of claim 1, wherein the plurality of volumetric and pressure-related parameters comprise a breaths per minute, a maximum pressure, an inspiratory time, an inspiratory time to expiratory time ratio (I-E ratio), a flow rate, percentage oxygen ($O_2$%), and/or a tidal volume.

3. The ventilation system of claim 2, wherein the tidal volume is a total volume of a single breath taken by a patient.

4. The ventilation system of claim 2, wherein the tidal volume is calculated using the equation:

$$\text{Tidal Volume} = \text{Inspiratory time} \times \text{Flow Rate}.$$

5. The ventilation system of claim 4, wherein the processor detects the tidal volume and adjusts the flow rate to maintain the breaths per minute, I-E ratio, and maximum pressure pre-set by the processor.

6. The ventilation system of claim 2, wherein the processor comprises operating the mechanical ventilator in one or more operational modes.

7. The ventilation system of claim 6, wherein the processor automatically adjusts values of one or more of the plurality of volumetric and pressure-related parameters when changing from one of the one or more operational modes to another one of the one or more operational modes.

8. The ventilation system of claim 6, wherein the one or more operational modes comprises at least one of the quick start mode, an automated pressure control mode, a volume assist control mode, a volume mode, a pressure control mode and a continuous positive airway pressure mode.

9. The ventilation system of claim 1, further comprising a pressurized gas source for providing low pressure oxygen to a patient.

10. The ventilation system of claim 1, further comprising a mask or other device adapted to fit over a patient's face and in communication with the mechanical ventilator for delivery of pressurized gas to the patient.

11. The ventilation system of claim 1, wherein the ventilation system comprises adult and child quick start buttons that initiate the mechanical ventilation function automatically through the single step operation, wherein the adult quick start button causes the quick start mode to initiate mechanical ventilation according to pre-set mechanical ventilation parameters for a typical adult individual and the child quick start button causes the quick start mode to initiate mechanical ventilation according to pre-set mechanical ventilation parameters for a typical child individual.

12. The ventilation system of claim 11, wherein the pre-set mechanical ventilation parameters for the typical adult individual comprises a maximum pressure in a range of about 15-60 cmH$_2$O, a breaths per minute in a range of about 6-15 breaths per minute, and an I-E ratio of about 1:2.

13. The ventilation system of claim 11, wherein the pre-set mechanical ventilation parameters for a typical child individual comprises a maximum pressure in a range of about 15-60 cmH$_2$O, a breaths per minute in a range of about 15-60 breaths per minute, and an I-E ratio of about 1:2.

14. The ventilation system of claim 1, further comprising a database operatively associated with the processor for storing values related to the plurality of the volumetric and pressure-related parameters.

15. The ventilation system of claim 1, further comprising:
wherein under the quick start mode, a first breath is delivered to a patient at a predetermined flow rate representative of the patient's tidal volume; and
wherein under the quick start mode the ventilator continuously detects change to the patient's tidal volume and the ventilator continuously adjusts the predetermined flow rate according to the changes to the patient's tidal volume in order to address changes to the patient's lung capacity automatically without intervention by a clinician.

16. The ventilation system of claim 1, wherein the quick start mode is further configured such that the non-clinician individual with no respiratory care expertise initiates the mechanical ventilation function automatically through the single step operation by actuating a single button.

17. A method for using a ventilation system comprising:
providing a ventilation system comprising:
a mechanical ventilator for providing pressurized gas to an airway of a patient based on a plurality of volumetric and pressure-related parameters, the mechanical ventilator being adapted to detect at least one of the plurality of volumetric and pressure-related parameters from the patient;
a processor in operative communication with the mechanical ventilator for receiving the at least one of the plurality of volumetric and pressure-related parameters from the patient and controlling the plurality of volumetric and pressure-related parameters;
a user interface in operative communication with the processor for displaying and adjusting values of the plurality of volumetric and pressure-related parameters; and
operating a quick start mode by the processor, wherein under the quick start mode the processor determines a tidal volume, continuously detects changes to the tidal volume, and adjusts a flow rate in response to the changes to the tidal volume, and wherein the quick start mode is configured to initiate automatically through a single step operation by a non-clinician individual with no respiratory care expertise such that the quick start mode is initiated and operated without assistance by a clinician,
wherein the processor disables the quick start mode after a first breath of a patient is detected by the processor to prevent the quick start mode from actuating parameters specific to the quick start mode after the first breath of the patient has been detected.

18. The method of claim 17, further comprising:
receiving the at least one of the plurality of volumetric and pressure-related parameters from the patient by the processor; and
adjusting another one of the plurality of volumetric and pressure-related parameters based on the detection of the at least one of the plurality of volumetric and pressure-related parameters from the patient, wherein the plurality of volumetric and pressure-related parameters comprise a breaths per minute, a maximum pressure, an inspiratory time, an inspiratory time to expiratory time ratio (I-E ratio), the flow rate, percentage oxygen (O$_2$%), and/or the tidal volume.

19. The method of claim 18, further comprising operating the mechanical ventilator by the processor in a plurality of operational modes.

20. The method of claim 19, wherein the processor includes a seamless mode transition function for seamless transition between one of the plurality of operational modes to another one of the plurality of operational modes.

21. The method of claim 19, wherein the plurality of operational modes comprises a volume control mode and a pressure control mode, wherein in a seamless mode transition function the processor makes adjustments for the maximum pressure and the flow rate when transitioning from the pressure control mode to the volume control mode by the processor.

22. The method of claim 17, wherein the ventilation system comprises adult and child quick start buttons that initiate the mechanical ventilation function automatically through the single step operation, wherein the adult quick start button causes the quick start mode to initiate mechanical ventilation according to pre-set mechanical ventilation parameters for a typical adult individual and the child quick start button causes the quick start mode to initiate mechanical ventilation according to pre-set mechanical ventilation parameters for a typical child individual.

* * * * *